United States Patent
Dominguez Valdes-Hevia et al.

(10) Patent No.: US 10,391,050 B2
(45) Date of Patent: Aug. 27, 2019

(54) DERMATOLOGICAL, COSMETIC OR COSMECEUTICAL COMPOSITIONS INTENDED FOR SKIN TREATMENT

(75) Inventors: Marta Dominguez Valdes-Hevia, Madrid (ES); Aurora Brieva Delgado, Madrid (ES); Salvador Gonzalez Rodriguez, Madrid (ES); Eduardo Reyes Martin, Madrid (ES); Jose Carballeira Morado, Santander (ES); Ernesto Quintana Gonzalez, Santander (ES); Juan Pablo Pivel Ranieri, Madrid (ES); Antonio Guerrero Gomez-Pamo, Madrid (ES); Angeles Juarranz De La Fuente, Madrid (ES); Jesus Espada Regalado, Madrid (ES); Francisco Sanz Rodriguez, Madrid (ES)

(73) Assignee: Industrial Farmacéutica Cantabria, S.A., Madrid (ES)

( * ) Notice: Subject to any disclaimer, the term of this patent is extended or adjusted under 35 U.S.C. 154(b) by 0 days.

(21) Appl. No.: 13/382,912

(22) PCT Filed: Jan. 28, 2010

(86) PCT No.: PCT/ES2010/000031
§ 371 (c)(1),
(2), (4) Date: Jan. 6, 2012

(87) PCT Pub. No.: WO2011/092350
PCT Pub. Date: Aug. 4, 2011

(65) Prior Publication Data
US 2012/0107410 A1    May 3, 2012

(51) Int. Cl.
*A61K 8/98* (2006.01)
*A61K 35/618* (2015.01)
*A61Q 19/08* (2006.01)

(52) U.S. Cl.
CPC ............ *A61K 8/987* (2013.01); *A61K 35/618* (2013.01); *A61Q 19/08* (2013.01)

(58) Field of Classification Search
USPC ........................................................ 424/547
See application file for complete search history.

(56) References Cited

U.S. PATENT DOCUMENTS 5,538,740 A * 7/1996 Abad .................... 424/547

FOREIGN PATENT DOCUMENTS

| CA | 2611645 | | 5/2009 |
|---|---|---|---|
| CN | 1205872 | | 1/1999 |
| CN | 1205872 | A * | 1/1999 |
| CN | 101468130 | | 1/2009 |
| CN | 101361758 | | 11/2009 |
| DE | 1813154 | A1 | 7/1970 |
| EP | 2085381 | | 5/2009 |
| FR | 2196747 | | 3/1974 |
| FR | 2594333 | | 8/1987 |
| FR | 2594333 | A1 * | 8/1987 |
| FR | 2595247 | A1 | 9/1987 |

OTHER PUBLICATIONS

Zwyer "Snail Caviar", Caviarist Blog, Mar. 17, 2009.*
Legand (FR 2594333A1) machine translation from Espacenet of disclosure.*
Legand (FR 2594333A1) machine translation from Espacenet of claims.*
"derived" Def. 1, Merraim Webster Online, Merriam Webster, n.d. Web. Jun. 2013.*
Murphy "Breeding and growing snails commercially in Australia", Report for the Rural Industries Research and Development Corporation, publication No. 00/188, Australian Government, 2001.*
Yang, CN 1205872, publication date Jan. 27, 1999, WIPO translation.*
Junginger H.E. (1992) Pharmaceutical Emulsions and Creams. In: Sjöblom J. (eds) Emulsions: A Fundamental and Practical Approach. NATO ASI Series (Series C: Mathematical and Physical Sciences), vol. 363. Springer, Dordrecht (Year: 1992).*
Yang CN 1205872 translation provided by LinguaLinx Language Solutions for the USPTO (Year: 1999).*
Perlmann, Gertrude E et al., "The Effect of Acetic Acid on the Stability of Serum Proteins," Medical Clinic, Massachusetts General Hospital, the Department of Medicine, Harvard Medical School, and the Massachusetts Department of Public Health, Boston, Dec. 1948, pp. 133-137.
Lehninger, Albert L., "The Molecular Basis of Cell Structure and Function," Biochemistry (second edition), The Johns Hopkins University School of Medicine, May 1976, pp. 62-63.

* cited by examiner

*Primary Examiner* — Emily A Cordas
(74) *Attorney, Agent, or Firm* — Jenkins, Wilson, Taylor & Hunt, P.A.

(57) ABSTRACT

The present invention relates to a product obtained from gastropod spawn, to be used to prepare dermatological, cosmetic or cosmeceutical compositions designed for skin care; said product has the capacity to activate and mobilize skin stem cells, as well as prevent the loss thereof that takes place as a consequence of chronological and premature ageing. The present invention also relates to the process followed in order to obtain said product.

10 Claims, 2 Drawing Sheets

DERMATOLOGICAL, COSMETIC OR COSMECEUTICAL COMPOSITIONS INTENDED FOR SKIN TREATMENT

The present invention relates to a product obtained from gastropod spawn, to be used in the preparation of dermatological, cosmetic or cosmeceutical compositions capable of activating and mobilising skin stem cells, as well as preventing the loss thereof that takes place as a consequence of chronological and/or premature ageing of the skin.

BACKGROUND OF THE INVENTION

The skin is the largest organ in the human, or animal, body. It acts as a protective barrier that isolates the body from the surrounding medium, protecting it and contributing to preserve its structures intact, whilst acting as a communication system with the environment. The skin has three layers: the epidermis, which is the most superficial layer, the dermis, which is the intermediate layer, and the hypodermis or subcutaneous tissue, which is the deepest layer of the skin.

Since it is the outermost organ, the skin is subjected to significant deterioration and aggression, which leads to premature ageing of the skin. The external factors that act thereon include excess solar radiation, atmospheric contamination, abusive use of surfactants, tobacco smoke, etc. But the skin may also suffer from premature ageing as a result of internal or endogenous factors, such as those related to an unbalanced nutrition in terms of vitamins, iatrogenic factors such as radiotherapy, the intake of drugs such as non-steroidal anti-inflammatory agents, immunosuppressants, etc., or the presence in the body of very reactive toxins such as those ingested by drug addicts, alcoholics, etc. Natural ageing also occurs as a consequence, for example, of the production of free radicals in the mitochondria, DNA alterations, etc.

Deterioration of the skin appears in the form of wrinkles, spots, laxity, benign neoplasms, etc.

Numerous cosmetic or pharmaceutical compositions have been disclosed for treatment of the skin, and the care and cleaning thereof, composed of very different ingredients, which include plant extracts and animal extracts. In this regard, one of the ingredients used in the preparation of skin care cosmetics have been gastropod secretions, what is commonly referred to as snail slime. Thus, for example, document DE1813154 discloses a composition designed for skin care that contains a fat and one or more active agents, which contains the slippery lubricating secretion excreted by a snail, particularly *Helix pomatia*. Patent FR2595247 discloses that extracts from the mucous membranes or digestive juices of gastropods are useful in cosmetics at concentrations ranging between 0.1%-10% due to their moisturising action on the epidermal surface. U.S. Pat. No. 5,538,740 discloses an active ingredient for cosmetic or therapeutic compositions obtained from the secretion of a centrifuged live gastropod, and said compositions may be applied to skin care.

On the other hand, document CA2611645 discloses the use of a *Helix aspersa* "snail slime" product to stimulate the proliferation of stem cells in vitro.

A stem cell is a cell that has the capacity to renew itself by means of mitotic divisions or to continue the differentiation pathway for which it is programmed. Moreover, it is capable of producing cells of one or more mature, functional, fully differentiated tissues, as a function of its degree of multipotentiality. Most of the tissues of an adult individual have their own specific population of stem cells which allow for their periodical renewal or their regeneration when tissue damage occurs. In particular, the epidermis undergoes constant renewal and consists of a stratified squamous epithelium associated with pilose follicles and sebaceous glands. These specialised structures are maintained by the self-renewal of epidermal stem cells and the differentiation of the offspring thereof. Skin stem cells are crucial for the healing of wounds and the regeneration of the skin and the hair. However, the capacity of stem cells may be diminished due to genetic problems, environmental influences and the ageing process. Therefore, the protection of stem cells is extremely important.

Although snail secretions are known to be useful for the preparation of skin cosmetics, thus far no product derived from snail spawn has been disclosed for the preparation of dermatological, cosmetic or cosmeceutical compositions that has a proven action on skin stem cells, activating and mobilising them, thereby preventing the loss thereof and, consequently, preventing and correcting ageing of the skin.

In this regard, the present invention discloses a product obtained from gastropod spawn for the preparation of cosmetic or cosmeceutical compositions which has been shown to have very beneficial effects on the skin, preventing and correcting the ageing thereof by acting directly on epithelial stem cells.

DESCRIPTION OF THE INVENTION

The object of the present invention consists of a product prepared from gastropod spawn of the family Helicidae, which is used for the preparation of dermatological, cosmetic or cosmeceutical compositions for the skin. Said product has the capacity to act on stem cells, activating and mobilising them, thereby preventing the loss thereof as a consequence of ageing of the skin caused by both endogenous and exogenous stressful factors.

The product is composed of organic and inorganic molecules from snail spawn, the organic molecules being polysaccharides, proteins, glycoproteins, peptides and amino acids, where the proteins and glycoproteins present a characteristic electrophoretic pattern, similar to that shown in FIG. 1, and the inorganic molecules being cations and anions such as phosphate, calcium, sodium, magnesium, iron, zinc, copper and selenium, in their most stable ion forms.

The product derived from snail spawn is used in the preparation of dermo-cosmetic compositions in the form of serum, solutions, injectables (monodose), gel (Hydragel), o/w gel-cream, w/o gel-cream, o/w cream, w/o cream, w/s cream, o/w/o cream, extemporaneous facial mask preparations, patches and, in general, all dermo-cosmetic (cosmeceutical) forms that may be used in the formulation of dermatological, cosmetic or cosmeceutical products. Said product, when applied in the form of a dermo-cosmetic composition, facilitates the rescue of skin stem cells intended to disappear due to senescence or endogenous or exogenous aggressions, and promotes the activation of said cells, as shown in Example 2 of the present specification. This activation is characterised by premature induction of DNA replication during cell division.

Moreover, said product, when applied in the form of a dermo-cosmetic composition, promotes the mobilisation of skin stem cells, which translates into the passage thereof from the basal area of pilose follicles to the interfollicular epithelium and distribution therein. The pilose follicle is the part of the skin where stem cells concentrate.

The spawn wherefrom the product of the present invention is prepared were obtained from gastropods grown in greenhouses protected from excess light, direct rain and aggressions by animals and insects. The climate and the protection offered by the greenhouse made it possible for the snails to be under optimal temperature and humidity conditions. The gastropods were fed with fodder, water and green plants, radishes and vegetables, and performed their natural hibernation and reproduction cycles.

The gastropods of the family Helicidae used for the preparation of the product in question are selected from the group that comprises *Helix aspersa, Helix pomatia, Helix lucarum, Helix lutescens, Helix hortensis, Helix aperta, Helix pisana, Otala punctata, Iberus gualtieranus alonensis, Helix nemoralis, Helix fructicola, Helix strigella, Helix fruticum, Helix bidens, Helix arbostorum, Helix rotundata, Helix aculeata, Helix pulchella, Helix personata, Helix holoserica, Helix alonensis* and *Helix candidissima*.

The process of obtaining the product derived from snail spawn of the present invention is described below. During their reproductive period, snails deposit their spawn in terracotta flower-pot receptacles containing soil sieved through 2-mm-pore sieves. Once the snail spawn have been laid, the collection phase is performed at an approximate temperature of 18° C.-24° C. and 60%-100% humidity. During this collection phase, the content of the flowerpots is deposited in 3-mm sieves, where the soil is cleaned and eliminated. The spawn are rinsed with distilled water at a very low pressure, such that, during the rinsings, all the soil goes through the sieve, leaving the spawn perfectly clean.

The spawn are immersed in saline solution and kept refrigerated at between 2° C. and 8° C. Subsequently, the saline solution is filtered through a mesh with a diameter of less than 3 mm, such that only intact snail spawn remain. The spawn are washed with purified water and, thereafter, are suspended, at a concentration ranging between 40% and 70% (w/w), in purified water, or saline solution, or a component or combination of components of the definitive dermo-cosmetic formulation; they are lysed and homogenised by means of a grinder, colloidal mill or in-line homogeniser; filtered through a 1-mm steel mesh, and the liquid thus obtained (product of the present invention) is used in the manufacturing of the suitable dermo-cosmetic preparations.

The final concentration of the product derived from snail spawn in the definitive dermo-cosmetic composition may range between 0.1% and 70% (w/w).

EXAMPLES

Figure 1:
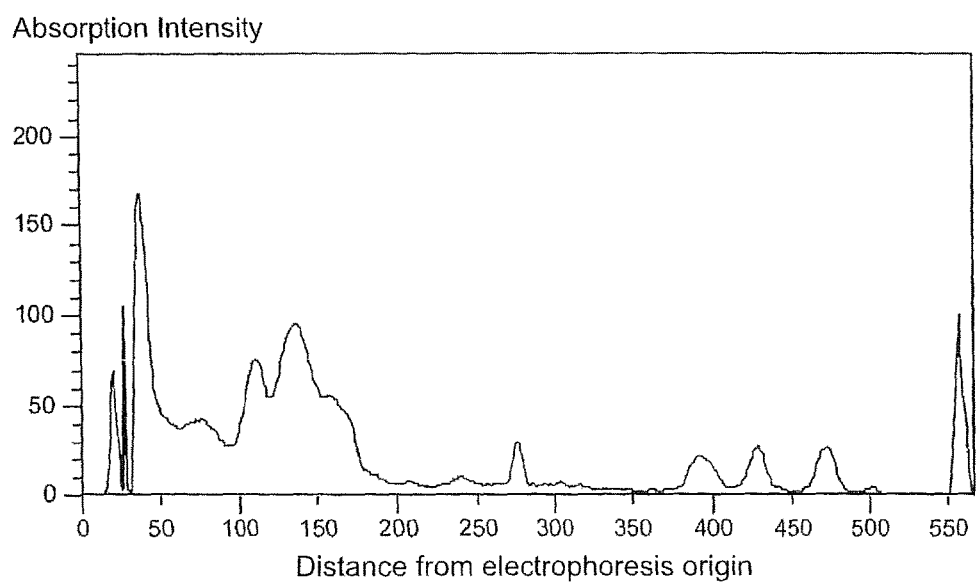
FIG. 1.—Densitometry and photograph of the polyacrylamide gel electrophoresis (SDS-PAGE) of the product derived from snail spawn, obtained as described in Example 1.
Figure 1:

Example 1: Preparation of the Product and of a Topical Composition that Contains it as an Active Ingredient During reproduction, snails deposit their spawn in flowerpots that contain soil sieved through 2-mm-pore sieves. Once the snail spawn have been laid, the collection phase is performed at an approximate temperature of 21° C. and approximately 80% humidity. During this collection phase, the content of the flowerpots is deposited in 3-mm sieves, where the soil is cleaned and eliminated. The spawn are rinsed with distilled water at a very low pressure, such that, during the rinsings, all the soil goes through the sieve, leaving the spawn perfectly clean.

The spawn are immersed in saline solution and kept refrigerated at between 2° C. and 8° C. Subsequently, the saline solution is filtered through a mesh with a diameter of less than 3 mm, such that only intact snail spawn remain. The spawn are washed with purified water and, thereafter, are suspended, at a concentration of 70% (w/w), in purified water; they are lysed and homogenised by means of a Silverson mill; they are filtered through a 1-mm steel mesh and the liquid thus obtained (product of the present invention) is used in the manufacturing of a cream, using it at a 70% concentration.

Example 2: Evaluation of the Activity of the Product Derived from Snail Spawn on the Dynamics of Skin Stem Cells Since stem cells in the adult epidermis divide infrequently, they are identified with cells that retain a specific DNA label (DNA label-retaining cells, LRCs). The cells that are undergoing division in an animal model (mouse) may be labelled by means of repeated pulses of bromodeoxyuridine (BrdU) or titriated $^3$H-thymidine. The label will be progressively lost following the successive divisions; however, keratinocytes that divide very infrequently (slow-cycling keratinocytes) retain the label for long periods of time (LRCs) (Bickenbach J R, McCutecheon J, Mackenzie I C. Rate of loss of tritiated thymidine label in basal cells in mouse epithelial tissues. Cell Tissue Kinet. 19(3): 325-333, 1986; Cotsarelis G, Sun T T, Lavker R M. Label-retaining cells reside in the bulge area of pilosebaceous unit: implications for follicular stem cells, hair cycle, and skin carcinogenesis. Cell. 61(7): 1329-1337, 1990). LRCs are preferably located in the bulge area, or prominent region, of the pilose follicles of the murine epidermis (Fuchs E, Tumbar T, Guasch G. Socializing with the neighbors: stem cells and their niche. Cell. 116(6): 769-778, 2004). The stem cells in the bulge are bipotential, since they may lead to both follicle keratinocytes and a cell population with a high division capacity, called transit-amplifying cells (TA). TAs migrate to the interfollicular epidermis and progressively show a lower differentiation potential; finally, they divide, leading to terminal differentiation keratinocytes. Occasionally, TAs have been considered to be stem cells, since they have a high proliferative potential. However, many authors indicate that only the cells in the bulge should be called stem cells, whereas those in the interfollicular epidermis would be the TAs.

The efficacy of the product derived from snail spawn, obtained as indicated in Example 1, was evaluated by applying it onto the skin of newborn C57BL/6 mice in the form of a cosmetic composition (cream).

The effect of the product in question on the proliferation and migration of epidermal stem cells was analysed; to this end, 30 newborn C57BL/6 mice were used, distributed in three groups, establishing a minimum of 5 animals per group:
Group C: Control (untreated animals).
Group M1: Animals treated with Sample 1 (cosmetic composition that contains the product derived from the snail spawn).
Group M2: Animals treated with Sample 2 (cosmetic composition with the same vehicle as Sample 1 which does not contain the product derived from the snail spawn).

The experiments were performed in accordance with the standards regulating the manipulation and protection of laboratory animals (Royal Decree 1201/2005).

The method used in this study to identify and quantify epidermal stem cells is based on the low proliferation frequency of this cell type with respect to the remaining cell populations in the tissue (Braun K M, Niemann C, Jensen U B, Sundberg J P, Silva-Vargas V, Watt F M. Manipulation of stem cell proliferation and lineage commitment: visualisation of label-retaining cells in wholemounts of mouse epidermis. Development. 130(21): 5241-5255, 2003).

Figure 2:
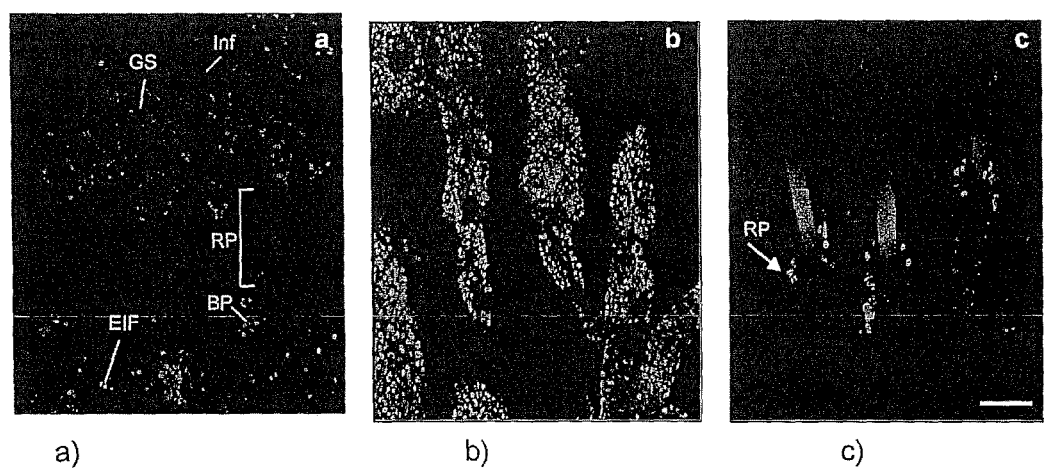
FIG. 2.—Labelling of the regions of the pilose follicle in the telogen phase by the incorporation of 5-bromo-2'-deoxyuridine (BrdU). Labelling at 24 h after injecting BrdU (FIG. 2a), following serial injections for 5 days (FIG. 2b) and once 70 days have elapsed since the last injection (FIG. 2c).

The cells undergoing division may be labelled by means of injections of tritiated thymidine ($[^3H]$thymidine) or 5-bromo-2'-deoxyuridine (BrdU), which are thymidine analogues, such that the labelled nucleotides are incorporated into the DNA replication process. After a short period of time (about 24 h) from the administration of a single dose of the analogue to an adult animal, the label is detected in the cells with the highest proliferation rate (FIG. 2a). The cells with the highest division rate are identified in the stratum basale of the interfollicular epidermis (IFE), sebaceous gland (SG), infundibulum (Inf) and, especially, the pilose bulb (BP), whereas the quiescent cells of the prominent region or "bulge" (PR) remain unlabelled (FIG. 2a). If the labelling injections are serial and sufficiently numerous, those cells with a low proliferation rate (potential adult stem cells) may also incorporate the label into the chromatin by means of processes other than replication, involved in the repair and maintenance of the DNA double strand (FIG. 2b). Several months after the last of the serial injections, the label is diluted in most cells as a result of the successive DNA replication cycles, whereas those cells with a minimal proliferation rate remain labelled for at least 10 weeks; for this reason, they are called label-retaining cells (LRCs). In the adult epidermis at rest, which primarily contains pilose follicles in the telogen or resting phase, the primary location of LRCs is the so-called prominent region ("bulge") of the pilose follicle (FIG. 2c).

Once a day, for four consecutive days, the 10-day-old mice received an injection of 5-bromo-2'-deoxyuridine (6.25 mg/ml, 50 mg/kg of body weight) in PBS phosphate buffer (137 mM NaCl, 2.7 mM KCl, 10 mM $Na_2HPO_4$, 2 mM $KH_2PO_4$), in order to label those cells that were in the DNA replication phase. Approximately 50 days after the labelling with BrdU, Samples 1 and 2, in their cream form, were topically applied twice a day, for 11 consecutive days, on the skin of the tails of the mice. Subsequently, these animals and their corresponding controls were sacrificed in a $CO_2$ chamber, in two different series for each group (five mice per group and series): immediately following the treatment, or ten days thereafter. Once the animals were sacrificed, the skin of the tail was processed in order to separate the epidermis and prepare in toto mounts. The method used to separate the epidermis from the dermis of the skin of the mice was based on that described by Braun et al. (Braun et al., Manipulation of stem cell proliferation and lineage commitment: visualisation of label-retaining cells in wholemounts of mouse epidermis. Development. 130 (21), 5241-5255, 2003). Once the tail was separated from the body, an incision was made, using a scalpel, in the ventral area, the skin being manually split in a single piece, which was incubated in 10 ml of 5 mM EDTA in PBS for 4 h at 37° C. Subsequently, the epidermis was carefully separated in a single sheet wherefrom the pilose follicles (PFs) hung, and fixed in formaldehyde (3.7% in PBS at 4° C.) for 48 h for the preparation of the in toto mounts. Finally, the epidermis sheets were abundantly washed with PBS phosphate buffer, stored in PBS with 0.2% sodium azide at 4° C. In order to prepare the in toto mounts, epidermis pieces of about 0.5×0.5 $cm^2$ were cut.

In order to identify and quantify the LRCs in the in toto mounts of the epidermis pieces, the BrdU-positive cells were located by means of immunofluorescence with the adequate antibodies. The samples were evaluated in a LEICA® TCS-SP2-AOBS spectral confocal microscope. The images were obtained using the LCS Suite software version 2.61 (LEICA®), which is an image processor and processed with the PHOTOSHOP® CS2 programme version 9.0.2 (ADOBE®), which is a photo editor software. The quantification of the number of LRCs was performed on the basis of the images obtained, considering a sample size of 30 follicles per mouse and a minimum of 5 mice per group. The results were expressed as mean values+/− standard deviation and the statistical analysis of the differences between the groups was performed using Student's T-test for independent samples, with the aid of the SPSS programme (version 15.0).

Figure 3:
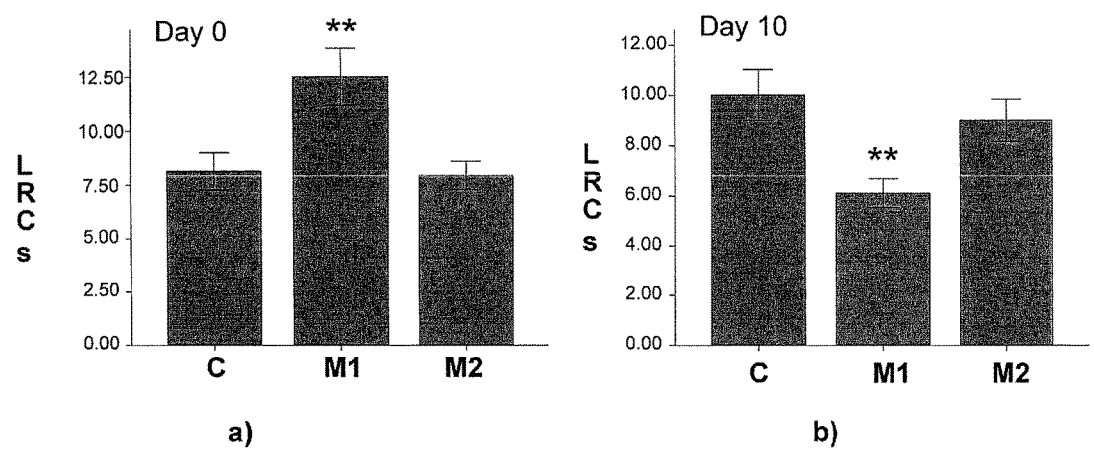
FIG. 3.—Representation of the quantification of potential epidermal stem cells (LRCs) (mean+/− standard error) in the prominent region of the pilose follicle on a sample of forty hairs pertaining to five or more animals in each case, quantified immediately following the treatments with or without the product derived from the gastropod spawn and at 10 days.

The results (FIG. 3) obtained show very significant differences in the number and distribution of LRCs, potential epidermal stem cells, in the mice treated with Sample 1 (group M1) with respect to the mice treated with Sample 2 (group M2) and the untreated control mice (group C). As described in the Methodology, the quantification of the LRCs per group was performed in two series, immediately following the treatment, or ten days thereafter, in order to evaluate the potential immediate effect of each sample on the epidermal stem cells, and the evolution thereof with time.

The quantification of LRCs immediately following the treatments showed a significant increase in LRCs in the prominent area ("bulge") of the pilose follicle in the mice of group M1, as compared to the mice of groups M2 and C (FIG. 3a). However, the quantification of LRCs 10 days after the treatments showed a significant reduction in the prominent region and an increase in the interfollicular epithelium in the mice of group M1 as compared to those in the other two groups (FIG. 3b).

These results are compatible with an activation of the epidermal stem cells residing in the pilose follicle induced by Sample 1. This activation would involve a premature induction of the replication of LRCs (increase in number in the prominent region at time 0) and a subsequent mobilisation and distribution in the interfollicular epithelium thereof (decrease in the number of LRCs in the prominent region at ten days). On the other hand, groups C and M2 slightly increase the number of resident LRCs in the prominent region as time passes. I.e. more LRCs are observed in both groups ten days after the end of the treatment as compared to the quantification performed in each group at day 0.

This observation shows that both groups behave with the expected physiological normality at 50 days of development, which entails a gradual mobilisation of their LRCs as a consequence of the beginning of the third normal hair cycle. This physiological mobilisation is not at all comparable to the very potent activation induced by Sample 1 and indicates that neither group C nor group M2 behave abnormally, as in the case of group M1.

Example 3: Chemical Description of the Product Derived from Snail Spawn

The product obtained from snail spawn, as described in Example 1, was physico-chemically and biologically analysed, and the following was determined: total protein content (according to the method described in: Lowry, O. H., H. J. Rosenbrough, A. L. Farr, R. J. Randall J. Biol. Chem. 193, 265-275. "Protein measurement with the Folin phenol reagent" (1951)), total sugars (according to the method described in: Dubois, A., K. A. Gilles, J. K. Hamilton, P. A. Rebers, F. Smith "Colorimetric method for the determination of sugars and related substances" Anal. Chem. 28, 350-356 (1956)), polyacrylamide gel electrophoresis analysis under denaturing conditions (U. K. Laemmli "Cleavage of structural proteins during the assembly of the head of the bacteriophage T4", Nature 227, 680-5 (1970)), amino acid content (according to the method described in: A. Novotny, "Basic Exercises in Immunochemistry", Springer-Verlag Berlin 1979, pp. 169-171), metal content (performed by the Interprofessional Dairy Laboratory of Cantabria (certified with no. EC-1988/05 for physico-chemical and microbiological analyses for Consumption, Cosmetic and Hygiene products), antioxidant activity (according to the method described in: Benzie, I. F., J. J. Strain "Ferric reducing/antioxidant power assay: direct measure of total antioxidant activity of biological fluids and modified version for simultaneous measurement of total antioxidant power and ascorbic acid concentration." Methods in enzymology, 299, pp. 15-27, 1999) and superoxide dismutase activity (according to the method described in: J. M. McCord, I. Fridowich "Superoxide Dismutase. An enzymic function for Erythrocuprein (Hemocuprein)", J. Biol. Chem. 244, 6049-6055 (1969)). The results are shown in Table 1 and Table 2.

TABLE 1

Analysis of the product derived from snail spawn

| Compound | Concentration or Activity |
| --- | --- |
| Total proteins | 243 mg/g |
| Total sugars | 284 mg/g |
| Antioxidant activity, FRAP (Ferric Reducing Antioxidant Potential) | 0.50% weight Trolox equivalent/weight |
| Superoxide Dismutase (SOD) Activity | 0.2 (% Weight SOD/Weight prot) |
| Amino acid content | 0.8 mg/ml |

Therefore, it has been shown that the snail spawn extract has a protein and sugar content, as well as superoxide dismutase activity. Moreover, it has been verified that it has antioxidant activity and fibroblast proliferative activity.

TABLE 2

Determination of metals on a sample of the product derived from snail spawn.

| Metal | Concentration |
| --- | --- |
| Phosphorus | 725 mg/l |
| Calcium | 567 mg/l |
| Sodium | 1445 mg/l |
| Magnesium | 54 mg/l |
| Iron | 4 mg/l |
| Zinc | 41 mg/l |
| Copper | <0.02 mg/l |
| Selenium | 0.304 µg/L |

From the above, it may be concluded that the product prepared from snail spawn contains both organic and inorganic molecules, the organic molecules being polysaccharides, proteins, glycoproteins, peptides and amino acids (Table 1). The inorganic substances are cations and anions derived from phosphorus (phosphates), calcium, sodium, magnesium, iron, zinc, copper and selenium, in their most stable ion forms (Table 2).

The invention claimed is:

1. A dermatological, cosmetic, or cosmeceutical composition designed for skin care, the composition being in a form selected from a group consisting of hydrogel, o/w gel cream, w/o gel cream, o/w cream, w/o cream, w/s cream, and o/w/o cream, said composition comprising a gastropod spawn extract isolated from lysed spawn of the Helicidae family and which comprises organic and inorganic molecules, wherein:
   (i) the organic molecules comprise polysaccharides, proteins, peptides and amino acids;
   (ii) the inorganic molecules comprise cations and anions derived from phosphorus, calcium, sodium, magnesium, iron, zinc, copper and selenium;
   (iii) the gastropod spawn extract is in a concentration that activates and mobilizes skin stem cells and prevents the loss thereof that takes place as a consequence of chronological and premature aging;
   (iv) the gastropod spawn extract has the characteristic electrophoretic fingerprint as shown in FIG. 1;
   (v) the gastropod spawn extract has superoxide dismutase activity; and
   (vi) the gastropod spawn extract is obtained by a process comprising:
      (a) manually collecting the gastropod spawn and eliminating soil content by sieving;
      (b) washing the gastropod spawn with distilled water, immersing the gastropod spawn in a saline solution and refrigerating the gastropod spawn at a temperature of between 2° C. and 8° C.;
      (c) washing the gastropod spawn with purified water to remove the saline solution;
      (d) suspending gastropod spawn at a concentration of between 40% and 70% by weight in purified water, a saline solution, or a component or combination of components of the dermatological, cosmetic, or cosmeceutical composition;
      (e) homogenizing the suspended gastropod spawn with a grinder, a colloidal mill, or an in-line homogenizer to produce a gastropod spawn extract; and
      (f) filtering the gastropod spawn extract through a 1-mm mesh to obtain a gastropod spawn extract.

2. The composition according to claim 1, wherein the gastropods are selected from the group: *Helix aspersa, Helix pomatia, Helix lucarum, Helix lutescens, Helix hortensis,*

*Helix aperta, Helix pisana, Otala punctata, Iberus gualtieranus alonensis, Helix nemoralis, Helix fructicola, Helix strigella, Helix fruticum, Helix bidens, Helix arbostorum, Helix rotundata, Helix aculeata, Helix pulchella, Helix personata, Helix holoserica, Helix alonensis* and *Helix candidissima*.

3. The composition according to claim 1, wherein said activation is due to a premature induction of replication.

4. The composition according to claim 1, wherein said mobilization of skin stem cells translates into the passage of the skin stem cells from the prominent area of the pilose follicle to the interfollicular epithelium and distribution therein.

5. The composition according to claim 1, wherein the extract from the gastropod spawn has a concentration ranging between 0.1% and 70% (w/w) of a total weight of the composition.

6. The composition according to claim 1, wherein the skin aging is produced by endogenous factors.

7. The composition according to claim 1, wherein the skin aging is produced by exogenous factors.

8. A dermatological, cosmetic, or cosmeceutical composition designed for skin care, the composition being in a form selected from a group consisting of hydrogel, o/w gel cream, w/o gel cream, o/w cream, w/o cream, w/s cream, and o/w/o cream, said composition comprising a gastropod spawn extract isolated from lysed gastropod spawn of the Helicidae family and which comprises organic and inorganic molecules, wherein:
  (i) the organic molecules comprise polysaccharides, proteins, peptides and amino acids;
  (ii) the inorganic molecules comprise cations and anions derived from phosphorus, calcium, sodium, magnesium, iron, zinc, copper and selenium;
  (iii) the gastropod spawn extract is in a concentration that activates and mobilizes skin stem cells and prevents the loss thereof that takes place as a consequence of chronological and premature aging;
  (iv) the gastropod spawn extract has superoxide dismutase activity; and
  (v) the gastropod spawn extract is obtained by a process comprising:
    (a) growing gastropods in a greenhouse, allowing for their natural hibernation and reproduction cycles, and making it possible for the gastropods to deposit their spawn in flowerpots filled with soil sieved through a 2-mm mesh;
    (b) manually collecting the gastropod spawn and eliminating soil content by sieving;
    (c) washing the gastropod spawn with distilled water, immersing the gastropod spawn in a saline solution and refrigerating the gastropod spawn at a temperature of between 2° C. and 8° C.;
    (d) washing the gastropod spawn with purified water to remove the saline solution;
    (e) suspending gastropod spawn at a concentration of between 40% and 70% by weight in purified water, a saline solution, or a component or combination of components of the dermatological, cosmetic, or cosmeceutical composition;
    (f) homogenizing the suspended gastropod spawn with a grinder, a colloidal mill, or an in-line homogenizer to produce a gastropod spawn extract; and
    (g) filtering the gastropod spawn extract through a 1-mm mesh to obtain a gastropod spawn extract.

9. The dermatological, cosmetic, or cosmeceutical composition of claim 8, wherein the dermatological, cosmetic, or cosmeceutical composition has antioxidant activity.

10. A process for preparing the composition of claim 1, the process comprising:
  (a) manually collecting the gastropod spawn and eliminating soil content by sieving;
  (b) washing the gastropod spawn with distilled water, immersing the gastropod spawn in a saline solution and refrigerating the gastropod spawn at a temperature of between 2° C. and 8° C.;
  (c) washing the gastropod spawn with purified water to remove the saline solution;
  (d) suspending gastropod spawn at a concentration of between 40% and 70% by weight in purified water, a saline solution, or a component or combination of components of the dermatological, cosmetic, or cosmeceutical composition;
  (e) homogenizing the suspended gastropod spawn with a grinder, a colloidal mill, or an in-line homogenizer to produce a gastropod spawn extract; and
  (f) filtering the gastropod spawn extract through a 1-mm mesh to obtain a gastropod spawn extract.

* * * * *